United States Patent [19]

Baugh, Jr. et al.

[11] 4,139,568

[45] Feb. 13, 1979

[54] PROCESS FOR MAKING METHYL FLUORIDE

[75] Inventors: Daniel W. Baugh, Jr.; Marylu B. Gibbs, both of Baton Rouge, La.

[73] Assignee: The Dow Chemical Company, Midland, Mich.

[21] Appl. No.: 908,308

[22] Filed: May 22, 1978

[51] Int. Cl.$^2$ .............................................. C07C 17/00
[52] U.S. Cl. ................................................. 260/653.7
[58] Field of Search ................... 260/653, 653.6, 653.7

[56] References Cited
U.S. PATENT DOCUMENTS 2,090,772  8/1937  Wiezevich ......................... 260/653.6

Primary Examiner—Delbert E. Gantz
Assistant Examiner—Joseph A. Boska

[57] ABSTRACT

Methanol and aqueous HF react in the vapor phase at 250° C.–400° C. in the presence of activated carbon, nickel fluoride, chromium fluoride, aluminum fluoride, or a mixture thereof to produce methyl fluoride plus dimethyl ether as the principal by-product.

5 Claims, No Drawings

PROCESS FOR MAKING METHYL FLUORIDE

BACKGROUND OF THE INVENTION

The present invention relates to a process for making methyl fluoride by the reaction of methanol and aqueous HF.

In the past, the fluorination of organic compounds by reaction with hydrogen fluoride has ordinarily been carried out under anhydrous conditions. Even under anhydrous conditions, many such attempted reactions have been found to be impractical or to be essentially inoperative. The preparation of alkyl fluorides by the reaction of primary alcohols with hydrogen fluoride in particular has been considered impossible in any practical sense although an old reference describes a partially successful pressure reaction of anhydrous HF with lower alcohols, see Meslans, Compte rend. 115, 1080 (1892). However, the water of reaction formed in the process caused the reaction to be reversible. Tertiary alkanols are known to react with aqueous hydrofluoric acid to produce the corresponding fluorides, see Cooper et al., J. Chem. Soc. 1937, 1185.

SUMMARY OF THE INVENTION

It has now been found that methanol can be successfully converted to methyl fluoride by contacting the vapors of methanol, hydrogen fluoride, and steam at about 250° C.–400° C. in the presence of a catalyst which is activated carbon, nickel fluoride, aluminum fluoride, chromium fluoride, or a mixture of two or more of these. Practically, this process involves use of a vaporized feed consisting of methanol and aqueous hydrogen fluoride.

DETAILED DESCRIPTION OF THE INVENTION

Preferably, the proportions of HF and steam used in the process are equivalent to using aqueous hydrofluoric acid of about 20–75 percent concentration. Usually the azeotropic composition containing about 35–40 percent by weight HF is most convenient.

The ratio of HF to methanol in the reaction mixture is not critical since the reaction will take place up to the extent of the minimum reactant present. However, an excess of HF is required to minimize the production of the dimethyl ether by-product and optimize the yield of methyl fluoride. About 1–6 moles of HF per mole of methanol is a preferred ratio and best results are usually obtained at an HF:methanol molar ratio of about 2–4:1.

The optimum temperature for the process varies according to the other reaction conditions and the particular catalyst used, but a temperature within the approximate range of 325° C.–375° C. is found to give the best results in most cases.

Although any metal fluoride will catalyze the reaction to some extent, for practical levels of conversion and yield of methyl fluoride, it is necessary to use a catalyst composed of one or more of nickel fluoride, chromium fluoride, aluminum fluoride, or activated carbon. Activated carbon is a less active catalyst for the reaction than the named metal fluorides but it provides relatively good yields. The best catalysts are obtained using activated carbon as a support for one or more of the metal fluorides, either the fluoride deposited on a granular carbon or a pelleted mixture of the two. The actual active catalyst in the case of the metal fluorides is thought to be an oxyfluoride or hydroxyfluoride which may be formed in the course of the fluorination reaction or by passing steam and HF through the catalyst bed either by reaction of water with a normal metal fluoride or by reaction of HF with an oxide, hydroxide, or carbonate, for example, such a compound deposited on activated carbon. Whatever the actual structure of such a fluoride catalyst, the terms nickel fluoride, chromium fluoride, and aluminum fluoride are used herein to include such oxygenated fluorides as well as the normal metal fluorides.

The residence time of the reactants in the catalyst bed is a noncritical factor of the process. A residence time of about 1–20 seconds is preferred and best results are obtained with a residence time of about 5–15 seconds.

The reaction with HF in the presence of water to produce the alkyl fluoride as the main product appears to be limited to methanol as higher primary alkanols react to make olefins or ethers as the principal products. This process offers the advantage that readily available and relatively cheap aqueous hydrofluoric acid is the fluorine source rather than the conventionally used anhydrous hydrogen fluoride that is required for most such fluorination reactions.

The product methyl fluoride is a valuable intermediate in the production of various chlorofluoromethanes which are useful propellants, refrigerants, and blowing agents for making foamed plastics.

The process is normally operated at or near atmospheric pressure. Moderate superatmospheric pressure can be employed for the reaction although this ordinarily confers little or no significant advantage.

EXAMPLE 1

The reactor was a 5 cm × 25 cm Monel metal tube packed with about 200 cc (350 g) of granular catalyst and horizontally disposed within a tubular electrical furnace. Methanol and 38 percent aqueous HF were mixed in the desired molar ratio and the solution was vaporized by pumping it through a coil of copper tubing heated at 150° C. by a sand bath. The vaporized feed then passed into the reactor. The effluent vapors were cooled by a water-cooled condenser and scrubbed with water before being sampled for gas chromatographic analysis. Total conversions and yields were determined by collecting and weighing liquid samples from the scrubber and measuring volumes of gaseous products by a wet test meter.

A catalyst consisting of 6 percent by weight Cr metal as $CrF_3$ on $AlF_3$ was prepared by wetting granular alumina with an aqueous solution of $CrCl_3$, vacuum drying the wet granules, and passing the vapors of 38 percent aqueous HF over the dried product at about 300° C. Methanol-aqueous HF mixtures in different molar ratios were passed through the reactor at 250° C. and a residence time of 9 seconds. Methanol was converted in the amount shown to a mixture consisting essentially of $CH_3F$ and dimethyl ether in each case.

TABLE 1

| Mole ratio, $HF/CH_3OH$ | 1.0 | 1.4 | 2.0 | 3.0 |
|---|---|---|---|---|
| % Yield $CH_3F$ | 33 | 43 | 72 | 74 |
| % Conversion, $CH_3OH$ | 2.6 | 2.3 | 4.8 | 9.6 |

EXAMPLE 2

The procedure of Example 1 was repeated using a 2:1 mole ratio of HF to methanol in the feed and varying the reactor temperature. The results are listed in Table 2.

TABLE 2

| Temp., °C. | 255 | 275 | 325 | 360 |
|---|---|---|---|---|
| % Yield CH$_3$F | 72 | 65 | 58 | 55 |
| % Conversion, CH$_3$OH | 4.8 | 12.4 | 15.5 | 27.5 |

The experiment was repeated with a 3:1 mole ratio of HF to methanol.

TABLE 3

| Temp., °C. | 255 | 275 | 320 |
|---|---|---|---|
| % Yield CH$_3$F | 74 | 72 | 70 |
| % Conversion, CH$_3$OH | 9.6 | 12.3 | 14.2 |

EXAMPLE 3

A superior catalyst was prepared by wetting 4–8 mesh Nuchar 503 activated charcoal (surface area about 1000 square meters per gram) with an aqueous solution of Cr(NO$_3$)$_3$ and Ni(NO$_3$)$_2$, vacuum drying the wet charcoal, roasting at about 300° C. to convert the nitrates to oxides, and passing vaporized 38 percent aqueous HF over the roasted product at about 300° C. The final catalyst contained 6 weight percent each of Cr and Ni as the fluorides. The mixed vapors of 38 percent aqueous HF and methanol at a 3:1 mole ratio HF to methanol were passed through the reactor at a rate calculated to give a residence time of about 8 seconds. The results obtained are listed in Table 4. Yields in Tables 4 and 5 represent weight percent concentrations in that effluent fraction.

TABLE 4

| Temp. | % Conversion | % Yield | | |
|---|---|---|---|---|
| °C. | CH$_3$OH | CH$_3$F | CH$_3$OCH$_3$ | CH$_4$ |
| 310 | 16 | 85 | 14 | 0.4 |
| 330 | 28 | 75 | 19 | 6 |
| 365 | 52 | 69 | 18 | 12 |
| 375 | 75 | 58 | 18 | 24 |

EXAMPLE 4

A catalyst consisting of 6 weight percent Cr as CrF$_3$ on activated charcoal was prepared by uniformly impregnating granular activated charcoal with an aqueous solution of CrCl$_3$, drying the impregnated charcoal, first in a rotary vacuum evaporator and finally in an oven at 150° C., then loading the dried material into the fluorination reactor as in Example 1 and passing vaporized 38 percent aqueous HF through it at about 300° C. until the CrCl$_3$ had been converted to the fluoride. The temperature in the catalyst bed rose to a peak of 377° C. during this procedure.

A feed mixture of vaporized 38 percent aqueous HF and methanol, HF:CH$_3$OH mole ration = 3:1, was passed through the catalyst bed at various temperatures with a residence time of about 8 seconds to obtain the following results.

TABLE 5

| Temp. | % Conversion | % Yield | | |
|---|---|---|---|---|
| °C. | CH$_3$OH | CH$_3$F | CH$_3$OCH$_3$ | CH$_4$ |
| 297 | 40 | 73 | 23 | 4 |
| 372 | 76 | 58 | 18 | 24 |
| 392 | >90 | 21 | 8 | 71 |

The activated charcoal support used for the catalyst in Examples 3 and 4 was tried as a catalyst at 300° C. and conditions otherwise as used in Example 3. Overall conversion was low but a high ratio of CH$_3$F to dimethyl ether was found in the converted product. At higher temperatures an increasing proportion of methane was produced.

When ethyl alcohol was substituted for methanol in the procedure of Example 1, the converted product was largely ethylene with little or no ethyl fluoride produced.

We claim:
1. A process for making methyl fluoride which comprises reacting by contacting methanol and hydrogen fluoride in the vapor phase in the presence of steam at about 250° C.–400° C. in the presence of a catalyst which is activated carbon, nickel fluoride, aluminum fluoride, chromium fluoride, or a mixture thereof.
2. The process of claim 1 wherein the HF and steam together are equivalent to vaporized aqueous HF of about 20–75 percent HF concentration.
3. The process of claim 2 wherein the temperature is about 325° C. –375° C.
4. The process of claim 2 wherein the molar ratio of HF to methanol is about 2-4:1.
5. The process of claim 2 wherein the proportion of HF to water is about that in 35–40 percent aqueous HF.

* * * * *